United States Patent [19]
Bickert et al.

[11] Patent Number: 4,864,026
[45] Date of Patent: Sep. 5, 1989

[54] METHOD OF MANUFACTURING N-ALKYL-N'-METHYL-ALKYLENEUREAS, PARTICULARLY N,N'-DIMETHYL-ALKYLENEUREAS

[75] Inventors: Peter Bickert, North Edison, N.J.; Hans Bellut, Duelmen, Fed. Rep. of Germany

[73] Assignee: HÜLS Aktiengesellschaft, Marl, Fed. Rep. of Germany

[21] Appl. No.: 144,231

[22] Filed: Jan. 15, 1988

[30] Foreign Application Priority Data

Feb. 5, 1987 [DE] Fed. Rep. of Germany ....... 3703389

[51] Int. Cl.$^4$ .................. C07D 233/34; C07D 239/10
[52] U.S. Cl. ..................................... 544/315; 548/317
[58] Field of Search ............... 548/318, 118, 321, 317; 544/315

[56] References Cited

U.S. PATENT DOCUMENTS 2,517,750  8/1950  Wilson .............................. 548/318
2,613,210 10/1952  Hurwitz et al. .................... 548/318

OTHER PUBLICATIONS

*Organic Reactions*, vol. 5, p. 301 (1949) "The Leuckart Reaction".

*Primary Examiner*—Richard A. Schwartz
*Assistant Examiner*—Richard A. Sharpe
*Attorney, Agent, or Firm*—Oblon, Spivak, McClelland, Maier & Neustadt

[57] ABSTRACT

A method of manufacturing N-alkyl-N'-methyl-alkyleneureas, by reacting an alkyleneurea with formaldehyde to produce a hydroxymethyl-alkyleneurea, and further reacting said hydroxymethyl-alkyleneurea with formic acid to yield a N-alkyl-N'-methyl-alkyleneurea product, wherein the molar ratio of the N-alkyl-N'-hydroxymethyl-alkyleneureas or N,N'-(bis)hydroxymethyl-alkyleneureas is from 1–2 to 1–10, preferably 1–4 to 1–7.

28 Claims, No Drawings

METHOD OF MANUFACTURING N-ALKYL-N'-METHYL-ALKYLENEUREAS, PARTICULARLY N,N'-DIMETHYL-ALKYLENEUREAS

BACKGROUND OF THE INVENTION

1. Field of the Invention

The invention relates to a method of manufacturing N-alkyl-N'-methyl-alkyleneureas, particularly N,N'-dimethyl-alkyleneureas, from the corresponding N-alkyl-N'-hydroxymethyl-alkyleneureas or N,N'-bis(hydroxymethyl)-alkyleneureas, by reaction with formic acid. Here "alkylene" means a bifunctional organic group, e.g., a 1,2-ethylene, or 1,3-propylene group. The preferred application of the method is in manufacturing N,N'-dimethyl-alkyleneureas.

The conversion noted above can be accomplished from the corresponding alkyleneureas and formaldehyde, or directly from urea and the corresponding diamine. It is unnecessary to isolate the N-alkyl-N'-hydroxymethyl-alkyleneurea or the N,N'-bis(hydroxymethyl)-alkyleneurea.

2. Discussion of the Background

There are known methods of manufacturing N,N'-dialkyl-alkyleneureas, having the following formula

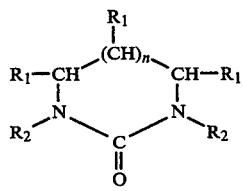

where $R_1$ represents H or $CH_3$, $R_2$ represents an alkyl group with 1 to 3 carbon atoms, and $n=0$ or 1. These methods comprise reacting an alkylnediol with an alkylamine and carbon dioxide at 150°–500° C. (Japanese No. 81-50565A); or reacting the corresponding alkylated alkylenediamine with phosgene (German AS No. 11 26 392); or alkylating the corresponding alkylenethiourea and hydrolyzing (1968, J. Med. Chem., 11, 214); or reducing a functionalized precursor where $R_1$ is alkoxy (German OS No. 15 45 613.

Practical commercial methods for converting alkyleneureas into the corresponding N,N'-dialkylalkyleneureas are not known, however. Alkyleneureas, e.g., ethyleneurea, are commercially available in industrial quantities (U.S. Pat. No. 2,497,309); and it is easy to prepare N-alkyl-N'-hydroxymethyl-alkyleneureas (or N,N'-bis(hydroxymethyl)alkyleneureas) from these alkyleneurea (U.S. Pat. No. 2,613,210). Accordingly, one faces the problem of how to convert N-alkyl-N'-hydroxymethyl-alkyleneureas or N,N'-bis(hydroxymethyl)-alkyleneureas into N-alkyl-N'-methyl-alkyleneureas or N,N'-dimethyl-alkyleneureas, respectively.

SUMMARY OF THE INVENTION

The present invention is a method of manufacturing N-alkyl-N'-methyl-alkyleneureas, particularly N,N'-dimethyl-alkyleneureas, having formula I

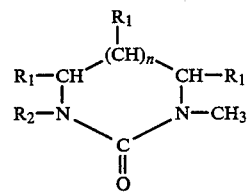

where $R_1$ represents H or $CH_3$, $R_2$ represents $CH_3$, $C_2H_5$, $C_3H_7$, or $C_4H_9$, and $n=0$ or 1, from the corresponding alkyleneureas, wherein the alkyleneurea precursors are reacted with formaldehyde to form the N-alkyl-N'-hydroxymethyl-alkyleneureas, particularly the N,N'-bis(hydroxymethyl)-alkyleneureas; characterized in that the N-alkyl-N'-hydroxymethyl-alkyleneureas (or N,N'-bis(hydroxymethyl)-alkyleneureas) are reacted with formic acid, wherein the molar ratio of the N-alkyl-N'-hydroxymethyl-alkyleneureas or N,N'-(bis)hydroxymethyl-alkyleneureas is from 1–2 to 1–10, preferably 1–4 to 1–7.

DETAILED DESCRIPTION OF THE PREFERRED EMBODIMENTS

A well proven method of reductive amination of aldehydes and ketones is the reaction known as the Leuckart-Wallach reaction, wherein carbonyl compounds are reacted with amines in the presence of formic acid (XI/1 Houben-Weyl p. 648 ff.). The Eschweiler-Clark variant of this reaction has become particularly important as a method of methylating amines by means of formaldehyde and formic acid (1949, Org. React., 5, 301). In this manner, e.g., ethylenediamine is converted to tetramethyl-ethylenediamine in high yield. In the same article (ibid, at 308), however, it is expressly stated that the reaction is not successful if polar groups are attached to the nitrogen, as is the case with urea. With such compounds, the product is said to be exclusively the hydroxymethyl derivative.

It is also known that hydroxymethyl-alkyleneureas such as N,N'-bis(hydroxymethyl)-ethyleneurea (formula I where $R_1$ is H, $R_2$ is $CH_2OH$, and $n=0$) or N,N'-bis(hydroxymethyl)-1,2-propyleneurea (formula I where $R_1$ is $CH_3$, $R_2$ is $CH_2OH$, and $n=0$) in the presence of formic acid react to form higher molecular weight products, with elimination of water, and this reaction can be utilized in treating cellulose (U.S. Pat. No. 2,613,210).

It has been discovered, surprisingly, in connection with the present invention, that N-alkyl-N'-hydroxymethyl-alkyleneureas, particularly N,N'-bis(hydroxymethyl)-alkyleneureas, can in fact be converted by formic acid to the corresponding N-alkyl-N'-methyl-alkyleneureas or N,N'-dimethyl-alkyleneureas, respectively. In the process, the formic acid acts as a reducing agent, being converted to carbon dioxide during the course of the reaction.

According to the present invention, in order to prepare N,N'-dimethyl-alkyleneureas, an N,N'-bis(hydroxymethyl)-alkyleneurea prepared from an alkyleneurea and formaldehyde is heated to 50°–150° C. with a twofold to tenfold molar amount of formic acid, without first having to be isolated. Preferably a molar ratio of formic acid to the N,N'-bis(hydroxymethyl)-alkyleneurea of 4:1 to 7:1 is employed. The reaction begins at 50° C., but it is advantageous to heat the mixture to boiling (about 100°–110° C. at normal pressure).

Alternatively, a higher temperature may be employed in an autoclave, with increased pressure.

After 6–16 hr following completion of the reaction, with the time depending on the temperature, the excess formic acid is distilled off from the reaction mixture, at normal or slightly reduced pressure. A certain amount of formic acid will remain in the reaction vessel because it is not completely separable from the N-alkyl-N'-methyl-alkyleneurea or N,N'-dimethyl-alkyleneurea.

To prepare the N-alkyl-N'-methyl-alkyleneurea or N,N'-dimethyl-alkyleneurea free from formic acid, the raw product is treated with a base, for example, an alkali hydroxide or carbonate or an alkaline earth hydroxide or carbonate and a highly pure product is distilled off, or alternatively a lower alcohol and catalytic amounts of a mineral acid are added to convert the formic acid into an ester which can be separated out by distillation.

In an advantageous variant of this method, the distillative recovery of the raw N-alkyl-N'-methyl-alkyleneurea or N,N'-dimethyl-alkyleneurea from the initial product mixture is dispensed with. Thus, it is possible to recover the desired pure dialkylalkyleneurea directly, in the reaction vessel, by adding the base or reacting with an alcohol, followed by distillation. This avoids an extraction step with the product mixture wherein the product mixture is extracted from aqueous solution by means of chloroform; such an extraction step is required in the manufacture of N,N'-dimethyl-alkyleneureas by alkylation and hydrolysis of alkylene-thioureas (1968, *J. Med. Chem.*, 11, 214).

It is possible to increase the yield of the inventive method by adding a certain amount of a base to the formic acid as early as the start of the reaction, to neutralize the acid. Preferred bases are alkali or alkaline earth salts of carboxylic acids. Sodium formate is particularly preferred. The base can be added in the amount of from 1 wt. % to the amount equivalent to the saturation concentration, particularly 5–30 wt. % on the basis of the formic acid added. The optimum added amount of sodium formate has been found to be 10–15 wt. % on the basis of the formic acid.

N-alkyl-N'-methyl-alkyleneureas and N,N'-dimethylalkyleneureas, particularly N,N'-dimethyl-ethyleneurea (1,3-dimethyl-imidazolidin-2-one) and N,N'-dimethyl-1,3-propyleneurea (1,3-dimethyl-tetrahydro-2(1H)-pyrimidinone), are important as polar aprotic solvents, among the uses of which are as recommended replacements for the carcinogenic hexamethylphosphoric triamide (1985, *Nachr. Chem. Technik u. Labor*, 33, 396; and 1985 (*Chemistry in Britain* 632).

Other features of the invention will become apparent in the course of the following descriptions of exemplary embodiments which are given for illustration of the invention and are not intended to be limiting thereof.

EXAMPLES

EXAMPLE 1a: Propyleneurea (tetrahydro-2(1H)-pyrimidinone)

126 g (2.10 mol) urea, 148 g (2.0 mol) propylenediamine, 120 g (1.94 mol) ethylene glycol, and 3 g (0.08 mol) NaOH were heated with stirring and with a slow stream of nitrogen being passed through the mixture. The temperature of the mixture was increased continuously from 115° C. to 160° C. over 2 hr. The mixture was then allowed to react for another 2 hr, was cooled down, and was suction filtered. The residue was washed with acetone and dried in vacuum. The ethylene glycol recovered could be reused for another reaction.

Yield: 184 g propyleneurea, corresponding to 92%
Melting point: 250°–60° C.
Analysis: C 48.0, H 8.1, N 28.3 (calculated 48.0, 8.0 and 28.0).

EXAMPLE 1b: Dimethylpropyleneurea (1,3-dimethyl-tetrahydro-2(1H)-pyrimidinone)

40 g (0.4 mol) propyleneurea and 92 g (2.0 mol) formic acid (100%, diluted to 85% with water) were charged to a reactor at 0° C. 28.8 g (0.96 mol) formaldehyde as a 36% formalin solution was added dropwise. $CO_2$ evolution began, in an exothermic reaction. After 1 hr at room temperature, the mixture was further heated 24 hr at 100°–105° C. After evaporation concentration, methanolic NaOH was added to neutralize, suction filtration was performed, and distillation was carried out at 1–0.001 torr. B.p.(2)=81°–83° C.

$n_D^{20} = 1.4888$. Purity determined by GC=99.2%.
Analysis: C 55.0, H 9.3, N 21.7, O 13.4, $H_2O$ 0.78 (calculated 56.3, 9.4, 21.9, 12.5, and 0).

EXAMPLE 2a: Ethyleneurea (imidazolidin-2-one)

Analogously to Example 1a, 63 g (1.05 mol) urea, 61.5 g (1.02 mol) ethylenediamine, 84 g (1.35 mol) ethylene glycol, and 1.5 g (0.04 mol) NaOH were reacted to a final temperature of 200° C., with further processing as in Example 1a. Because ethyleneurea is substantially soluble in ethylene glycol, good yields are achieved only if the ethylene glycol is recycled; accordingly, this was done.

Yield: 75.2 g ethyleneurea, corresponding to 87.4% yield. B.p.=130° C.
Analysis: C 41.7, H 7.1, N 32.6, O 19.0 (calculated 41.8, 7.0, 32.6, and 18.6).

EXAMPLE 2b: N,N'-Dimethyl-ethyleneurea (1,3-dimethylimidazolidin-2-one):

Analogously to Example 1b, 43 g (0.5 mol) ethyleneurea was reacted with 135 g (2.35 mol) 85% formic acid and 90 ml (1.11 mol) 37% formalin, with further processing as per Example 1b. B.p. (3)=70°–72° C.

Yield: 44.5 g N,N'-dimethyl-ethyleneurea, corresponding to 78%.
$n_D^{20} = 1.4724$. Purity determined by GC=99.8%.
Analysis: C 51.0, H 8.9, N 24.4, O 16.0, $H_2O$ 0.3 (calculated 52.6, 8.8, 24.6, 14.0, 0).

EXAMPLE 3

64 g (0.44 mol) 1,3-bis(hydroxymethyl)-imidazolidin-2-one was heated 8 hr at reflux with 124 g (2.7 mol) formic acid. Then 86 g formic acid was distilled off under reduced pressure. The residue was added to 150 ml 20% sodium hydroxide, and extracted three times with 50 ml chloroform each time. The combined organic phase was dried with sodium sulfate and concentrated by evaporation. Vacuum distillation of the residue gave, at 85°–90° C. and 2 torr, 28 g 1,3-dimethyl-imidazolidin-2-one, of purity >99% by GC and $^1$H-NMR. Yield=56%.

EXAMPLE 4

320 g (2.2 mol) 1,3-bis(hydroxymethyl)-imidazolidin-2-one and 200 g (2.9 mol) sodium formate were dissolved in 620 g (13.5 mol) formic acid and heated 8 hr at reflux. Then 238 g formic acid was distilled off under reduced pressure, and 200 g potassium carbonate was added portionwise to the residue. After cooling, the raw product was decanted from the salts which had precipitated, was washed with a small amount of methylene chloride, and was distilled in vacuum. 157 g 1,3-dimethyl-imidazolidin-2-one was obtained at 90°–95° C. and 3 torr. Yield=63%. Purity>98% by GC and $^1$H-NMR.

EXAMPLE 5

147 g (1.0 mol) 1,3-bis(hydroxymethyl)-imidazolidin-2-one and 9 g (0.1 mol) sodium formate were heated in 95 g (2.0 mol) formic acid 9 hr under reflux. After distillative separation of most of the unreacted formic acid, 23 g of a formic-acid-containing raw product was obtained at 70°–72° C. and 1 torr. Subsequent vacuum distillation resulted in 16 g 1,3-dimethyl-imidazolidin-2-one of purity>98% as determined by GC and $^1$H-NMR. Yield=14%.

EXAMPLE 6

147 g (1.0 mol) 1,3-bis(hydroxymethyl)-imidazolidin-2-one and 54 g (0.8 mol) sodium formate were heated with 570 g (12.4 mol) formic acid 9 hr under reflux. Then 425 g formic acid was distilled off under reduced pressure, and 800 g methanol and 48 g conc. sulfuric acid were added to the residue. The mixture was heated 3 hr under reflux, the sodium sulfate formed was filtered out, and the filtrate was evaporation concentrated. Distillation of the residue in vacuum gave 80 g 1,3-dimethyl-imidazolidin-2-one at 90°–95° C. and 3 torr. Purity>98% by GC and $^1$H-NMR. Yield=70%.

EXAMPLE 7

The procedure was as in Example 6, but with longer reaction times. For reaction time 8 hr, 97 g 1,3-dimethyl-imidazolidin-2-one was obtained (85% yield), and for 16 hr, 98 g (86% yield).

EXAMPLE 8

A mixture of 29.4 g (0.20 mol) 1,3-bis(hydroxmethyl)-imidazolidin-2-one, 115.0 g (2.5 mol) formic acid, and 10.2 g (0.15 mol) sodium formate was heated at 150° C. in an autoclave for 1.5 hr. After treatment with 200 ml methanol and 9 g sulfuric acid as in Example 6, 16.4 g 1,3-dimethyl-imidazolidin-2-one was obtained. Purity>98% by GC and $^1$H-NMR. Yield=72%.

EXAMPLE 9

The procedure was as in Example 8, but with reaction times of 4 and 8 hr. Yields were 18.0 g (79%) and 16.2 g (71%), respectively.

EXAMPLE 10

80 g (0.5 mol) 1,3-bis(hydroxymethyl)-tetrahydro-2-(1H)-pyrimidinone and 27 g (0.4 mol) sodium formate were heated with 272 g (5.9 mol) formic acid for 8 hr under reflux. Then 194 g formic acid was distilled off under reduced pressure, and 400 ml methanol and 17 g conc. sulfuric acid were added to the residue. The mixture was heated 3 hr under reflux, the sodium sulfate which formed was removed by suction filtration, and the filtrate was evaporation concentrated. Vacuum distillation of the residue yielded 51 g 1,3-dimethyl-tetrahydro-2(1H)-pyrimidinone at 85°–90° C. and 1 torr. Purity was >98% by GC and $^1$H-NMR. Yield=80%.

EXAMPLE 11

The procedure was as in Example 10, but the starting material was 80 g (0.5 mol) 1,3-bis(hydroxymethyl)-4-methyl-imidazolidin-2-one. The product was 47 g 1,3,4-trimethyl-imidazolidin-2-one, b.p. 62°–64° C. at 10.5 torr. Purity>98% by GC and $^1$H-NMR. Yield=71%.

EXAMPLE 12

The procedure was as in Example 10, but the starting material was 103 g (0.5 mol) 1,3-bis(hydroxymethyl)-4,4,6-trimethyl-tetrahydro-2(1H)-pyrimidinone. The product was 66 g 1,3,4,4,6-pentamethyl-tetrahydro-2(1H)-pyrimidinone, b.p. 97°– 101° C. at 0.4 torr, m.p. 36.5° C. Purity>98% by GC and $^1$H-NMR. Yield=76%.

EXAMPLE 13

72 g (0.5 mol) 1-ethyl-3-hydroxymethyl-imidazolidin-2-one and 14 g (0.2 mol) sodium formate were heated with 138 g (6.0 mol) formic acid for 8 hr under reflux. Then 95 g formic acid was distilled off under reduced pressure, and 200 ml methanol and 8 g conc. sulfuric acid were added to the residue. The mixture was heated 3 hr under reflux, the sodium sulfate formed was removed by suction filtration, and the filtrate was evaporation concentrated. Distillation of the residue in vacuum yielded 46 g 1-ethyl-3-methyl-imidazolidin-2-one at 80°–84° C. and 0.8 torr. Purity>98% by GC and $^1$H-NMR. Yield=72%.

EXAMPLE 14

The procedure was as in Example 13, except that the starting materials were as follows:

(a) 79 g (0.5 mol) 1-n-propyl-3-hydroxymethyl-imidazolidin-2-one (instead of the 1-ethyl). The product was 48 g 1-methyl-3-n-propyl-imidazolidin-2-one, b.p. 88°–91° C. at 1.0 trr. Yield=68%.

(b) 79 g (0.5 mol) 1-i-propyl-3-hydroxymethyl-imidazolidin-2-one (instead of the 1-ethyl). The product was 43 g 1-methyl-3-i-propyl-imidazolidin-2-one, b.p. 83°–87° C. at 0.9 torr. Yield=61%.

(c) 86 g (0.5 mol) 1-t-butyl-3-hydroxymethyl-imidazolidin-2-one (instead of the 1-ethyl). The product was 33 g 1-methyl-3-t-butyl-imidazolidin-2-one, b.p. 96°–100° C. at 1.2 torr. Yield=42%.

(d) 93 g (0.5 mol) 1-t-butyl-3-hydroxymethyl-tetrahydro-2(1H)-pyrimidinone (instead of the 1-ethyl-3-hydroxymethyl-imidazolidin-2-one). The product was 38 g 1-t-butyl-3-methyl-tetrahydro-2(1H)-pyrimidinone, b.p. 100°–103° C. at 1.1 torr. Yield=45%.

Purities of 14(a, b, c, and d) were>98% by GC and $^1$H-NMR.

Obviously, numerous modifications and variations of the present invention are possible in light of the above teachings. It is therefore to be understood that within the scope of the appended claims, the invention may be practiced otherwise than as specifically described herein.

What is claimed is:

1. A method of manufacturing an N-alkyl-N,-methyl-alkyleneureas of the formula

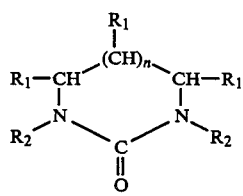

wherein $R_1$ is H or $CH_3$, $R_2$ is $CH_3$, $C_2H_5$, $C_3H_7$, or $C_4H_9$, and n is 0 or 1, comprising the steps of:

reacting a hydroxymethyl-alkyleneurea selected from the group consisting of N,N'-bis(hydroxymethyl)-alkyleneurea and N-alkyl-N'-hydroxymethyl-alkyleneureas, the alkyl group having 1-4 carbon atoms, with formic acid to yield said N-alkyl-N'-methyl-alkyleneurea, wherein the molar ratio of said hydroxymethyl-alkyleneurea to said formic acid is from 1:2 to 1:10.

2. The method of claim 1, wherein said N-alkyl-N'-methyl-alkyleneurea is a N,N'-dimethyl-alkyleneurea.

3. The method of claim 1, wherein said reacting step is conducted at an elevated pressure.

4. The method of claim 1, wherein said reacting step is conducted at atmospheric pressure.

5. The method of claim 1, wherein said reacting step is conducted at a temperature between about 50°–150° C.

6. The method of claim 5, wherein said reacting step is conducted at a temperature of about 100°–110° C. at atmospheric pressure.

7. The method of claim 1, wherein said mole ratio is 1:4 to 1:7.

8. The method of claim 1, wherein a base is added to the reaction mixture comprising said hydroxymethyl-alkyleneurea and formic acid during said reacting step.

9. The method of claim 8, wherein said base is an alkali, or alkaline earth salt of a carboxylic acid.

10. The method of claim 9, wherein said base is sodium formate.

11. The method of claim 8, wherein said base is added to said reaction mixture in an amount between 1 wt. % of the formic acid used and the saturation concentration.

12. The method of claim 11, wherein said base is added in an amount between about 5–30 wt. % of the formic acid used.

13. The method of claim 12, wherein said base is added in an amount of about 10–15 wt. % of the formic acid used.

14. The method of claim 19, wherein said hydroxymethyl-alkyleneurea produced in said reacting step with formaldehyde is further reacted with said formic acid without further purification or preliminary processing.

15. The method of claim 1, wherein said N-alkyl-N'-methyl-alkyleneurea product contains residual formic acid and further comprising:

eliminating said residual formic acid by contacting said product with an alkali or alkaline earth metal hydroxide or carbonate.

16. The method of claim 1, wherein said N-alkyl-N'-methyl-alkyleneurea product contains residual formic acid and further comprising:

eliminating said residual formic acid by reacting said residual formic acid with a low-boiling alcohol in the presence of a mineral acid to form a formate ester; and distilling said formate ester from said product.

17. The method of claim 16, wherein said low-boiling alcohol is methanol.

18. The method of claim 1, further comprising:

distilling said N-alkyl-N'-methyl-alkyleneurea from said product.

19. The method according to claim 1, wherein said hydroxymethyl-alkyleneurea is prepared by reacting an alkyleneurea or an N-alkyl-alkyleneurea with formaldehyde.

20. The method according to claim 1, wherein said hydroxymethyl-alkyleneurea is 1,3-bis(hydroxymethyl)-imidazolidin-2-one.

21. The method according to claim 1, wherein said hydroxymethyl-alkyleneurea is 1,3-bis(hydroxymethyl)-tetrahydro-2-(1H)-pyrimidinone.

22. The method according to claim 1, wherein said hydroxymethyl-alkyleneurea is 1,3-bis(hydroxymethyl)-4-methyl-imidazolidin-2-one.

23. The method according to claim 1, wherein said hydroxymethyl-alkyleneurea is 1,3-bis(hydroxymethyl)-4,4,6-trimethyl-tetrahydro-2(1H)-pyrimidinone.

24. The method according to claim 1, wherein said hydroxymethyl-alkyleneurea is 1-ethyl-3-hydroxymethyl-imidazolidin-2-one.

25. The method according to claim 1, wherein said hydroxymethyl-alkyleneurea is 1-n-propyl-3-hydroxymethyl-imidazolidin-2-one.

26. The method according to claim 1, wherein said hydroxymethyl-alkyleneurea is 1-i-propyl-3-hydroxymethyl-imidazolidin-2-one.

27. The method according to claim 1, wherein said hydroxymethyl-alkyleneurea is 1-t-butyl-3-hydroxymethyl-imidazolidin-2-one.

28. The method according to claim 1, wherein said hydroxymethyl-alkyleneurea is 1-t-butyl-3-hydroxymethyl-tetrahydro-2(1H)-pyrimidinone.

* * * * *